US00PP22806P3

(12) United States Plant Patent

Sandler-Ziv et al.

(10) Patent No.: US PP22,806 P3

(45) Date of Patent: Jun. 19, 2012

(54) *HIPPEASTRUM* PLANT NAMED 'RUBY STAR'

(50) Latin Name: *Hippeastrum Herb.*
Varietal Denomination: RUBY STAR

(75) Inventors: Dorit Sandler-Ziv, Nes Ziona (IL); Avner Cohen, Nes Ziona (IL); Aurel Ion, Rehovot (IL); Corneliu Fintea, Azur (IL); Marina Baizerman, Bat Yam (IL); Ahuva Daous, Mazkeret Batia (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 247 days.

(21) Appl. No.: 12/657,904

(22) Filed: Jan. 29, 2010

(65) Prior Publication Data

US 2011/0191926 P1 Aug. 4, 2011

(51) Int. Cl.
*A01H 5/00* (2006.01)

(52) U.S. Cl. ..... Plt./402

(58) Field of Classification Search ..... Plt./402
See application file for complete search history.

(56) References Cited

U.S. PATENT DOCUMENTS

| | | | | | |
|---|---|---|---|---|---|
| PP10,373 | P | * | 5/1998 | Barnhoorn | Plt./402 |
| PP10,374 | P | * | 5/1998 | Barnhoorn | Plt./402 |
| PP12,469 | P2 | * | 3/2002 | Meerow | Plt./402 |
| PP12,562 | P2 | * | 4/2002 | Meerow | Plt./402 |
| PP12,633 | P2 | * | 5/2002 | Meerow | Plt./402 |

* cited by examiner

*Primary Examiner* — Wendy C Haas

(74) *Attorney, Agent, or Firm* — Foley & Lardner LLP

(57) ABSTRACT

A new and distinct *Hippeastrum* interspecific hybrid plant named 'RUBY STAR' particularly characterized by star-shaped flower, measuring 18 cm to 20 cm in length and 14 to 17 cm in diameter, and with a unique color pattern of primarily dark red (RHS 53 B) with yellow-greenish (RHS 145 B) stripes and greyed-purple (RHS 183 B) veining.

5 Drawing Sheets

Botanical name of the genus of the Interspecific Cross of the plant claimed: *Hippeastrum Herb,*. syn. *Amaryllis*
Variety denomination: 'RUBY STAR'.

BACKGROUND OF THE INVENTION

The present invention relates to a new and distinct interspecific hybrid variety of *Hippeastrum,* botanically known as *Hippeastrum Herb.,* syn. *Amaryllis*, of the Amaryllidaceae family, and hereinafter referred to by the name 'RUBY STAR'. The *Hippeastrum* genus is native to tropical and subtropical regions of South America and the Caribbean, and includes more than 80 different species and several hundred hybrids.

The new *Hippeastrum* 'RUBY STAR' is a product of a controlled breeding program conducted by the inventors, Dorit Sandler-Ziv, Corneliu Fintea, Aurel Ion, Avner Cohen, Marina Baizerman and Ahuva Daous, in Bet-Dagan, Israel. The objective of the breeding program was to develop a new *Hippeastrum* variety with excellent ornamental characteristics, adapted to bulb production under Israeli climatic conditions and suitable for both cut flower and pot production worldwide.

The new *Hippeastrum* 'RUBY STAR' originated from a cross made by the inventors in 2000 in Bet-Dagan, Israel. The female or seed parent is the unpatented, wild-type *Hippeastrum papillio* designated WT30. The male or pollen parent is the unpatented, interspecific *Hippeastrum* hybrid designated 97/4 (*H. vittatum* 'WHITE'×wild-type *H. cybister* designated WT40). The new *Hippeastrum* 'RUBY STAR' was selected by the inventors as a single flowering plant from the progeny of the stated cross in a controlled environment in 2003 in Bet-Dagan, Israel.

Asexual propagation of the new *Hippeastrum* 'RUBY STAR' using the "twin-scaling" method (division of the mother bulb into about 12 vertical segments which are subsequently subdivided into 5 to 6 twin-scale units) was first performed in September, 2004, in Bet-Dagan, Israel. The twin-scale units are dipped for 15 minutes in 0.2% BENLATE and 0.5% MARPAN to prevent fungal infection, then the segments are air dried for 3-4 hours and placed in moist Vermiculite no. 2 (8% to 10% moisture) and incubated at 22° C. to 24° C. for 3 to 4 months. The resulting bulblets are planted in coco-peat and Tuff 0.8 (80:20%) and grown for 2 years until they flower for the first time. Of the twin scales first propagated in September, 2004, the resulting bulbs first flowered in the winter of 2007, and demonstrated that the combination of characteristics as herein disclosed for the new variety is firmly fixed and retained through successive generations of asexual propagation. The new variety propagates true-to-type.

BRIEF DESCRIPTION OF THE INVENTION

The following traits have been repeatedly observed and are determined to be characteristics of 'RUBY STAR', which in combination distinguish this *Hippeastrum* as a new, unique and distinct variety:

1. star-shaped flower, measuring about 18 to 20 cm in length and about 14 to 17 cm in diameter, and with a unique color pattern of primarily dark red (RHS 53 B) with yellow-greenish (RHS 145 B) stripes and greyed-purple (RHS 183 B) veining.

Plants of the new *Hippeastrum* 'RUBY STAR' differ from plants of the female or seed parent, the unpatented, wild-type

*Hippeastrum papillio* designated WT30, in the following characteristics described in Table 1.

TABLE 1

| Characteristic | New Cultivar 'RUBY STAR' | Female Parent H. papillio WT30 (unpatented) |
|---|---|---|
| Plant Height | 45 cm to 70 cm | 18 cm to 24 cm |
| Number of flowers per inflorescence | 4 to 5 | 2 to 3 |
| Outer tepal shape | Ovate | Oblanceolate |
| Outer tepal, Upper side Main color | Red | Whitish |
| Outer tepal, Upper side Secondary vein | Dark greyed-purple | Maroon red |

Of the many commercial cultivars known to the present inventor, the most similar to the new *Hippeastrum* 'RUBY STAR' is the *Hippeastrum* hybrid (leopoldii-type) 'Red Lion' (unpatented), and differs from the new *Hippeastrum* 'RUBY STAR' in the following characteristics described in Table 2:

TABLE 2

| Characteristic | New Cultivar 'RUBY STAR' | Comparison Cultivar 'Red Lion' (patented) |
|---|---|---|
| Plant height | 45 cm to 70 cm | 38 cm to 60 cm |
| Number of stems per bulb per year | 1 to 3 | 2 to 3 |
| Scape length | 45 cm to 60 cm | 38 cm to 50 cm |
| Number of flowers per inflorescence | 4 to 5 | 2 to 4 |
| Flower Shape | Star shape | Rounded |
| Flower length | 18 cm to 20 cm | 16 cm to 18 cm |
| Flower Throat | Covered with numerous green-white and greyed-purple hairs | Covered with numerous white and yellowish hairs |
| Outer tepal, Upper side Main color | Red, RHS 53 B | Red, RHS 43 A |
| Outer tepal, Under side Main color | Red with yellow-green stripes | Glossy red with short greenish veins |
| Filament | | |
| Color of upper part | Very light green | Red |
| Color of lower part | Yellow-green | Red |
| Anther color | Yellow-greenish | Light yellow |
| Fruit/Seed | None | Present |

BRIEF DESCRIPTION OF THE PHOTOGRAPHS

The accompanying photographs illustrate the overall appearance of the new *Hippeastrum* variety 'RUBY STAR' showing the colors as true as is reasonably possible with colored reproductions of this type. Colors in the photographs may differ slightly from the color values cited in the detailed botanical description, which accurately describe the color of 'RUBY STAR'.

DETAILED BOTANICAL DESCRIPTION

Figure 1:
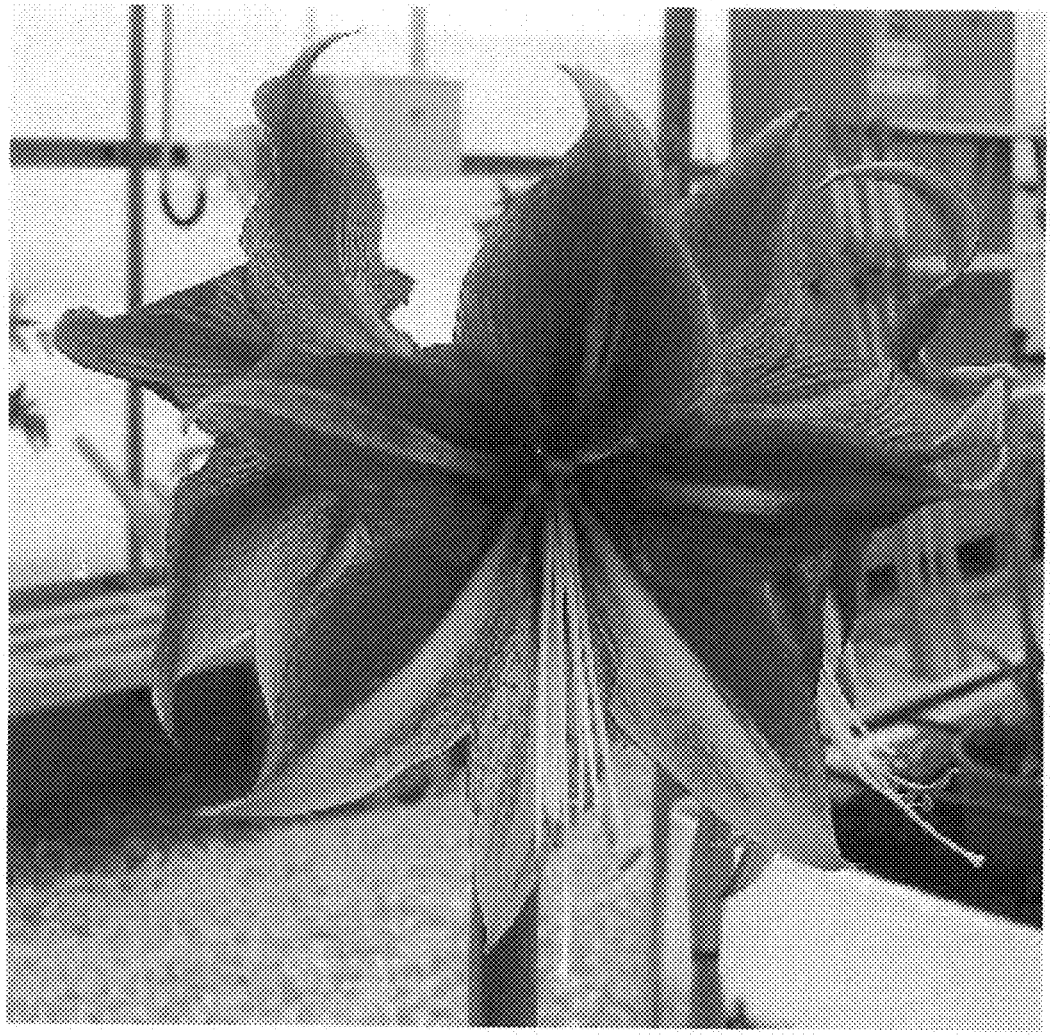
FIG. 1 shows a close-up side view of a typical fully open flower of 'RUBY STAR'.
Figure 2:
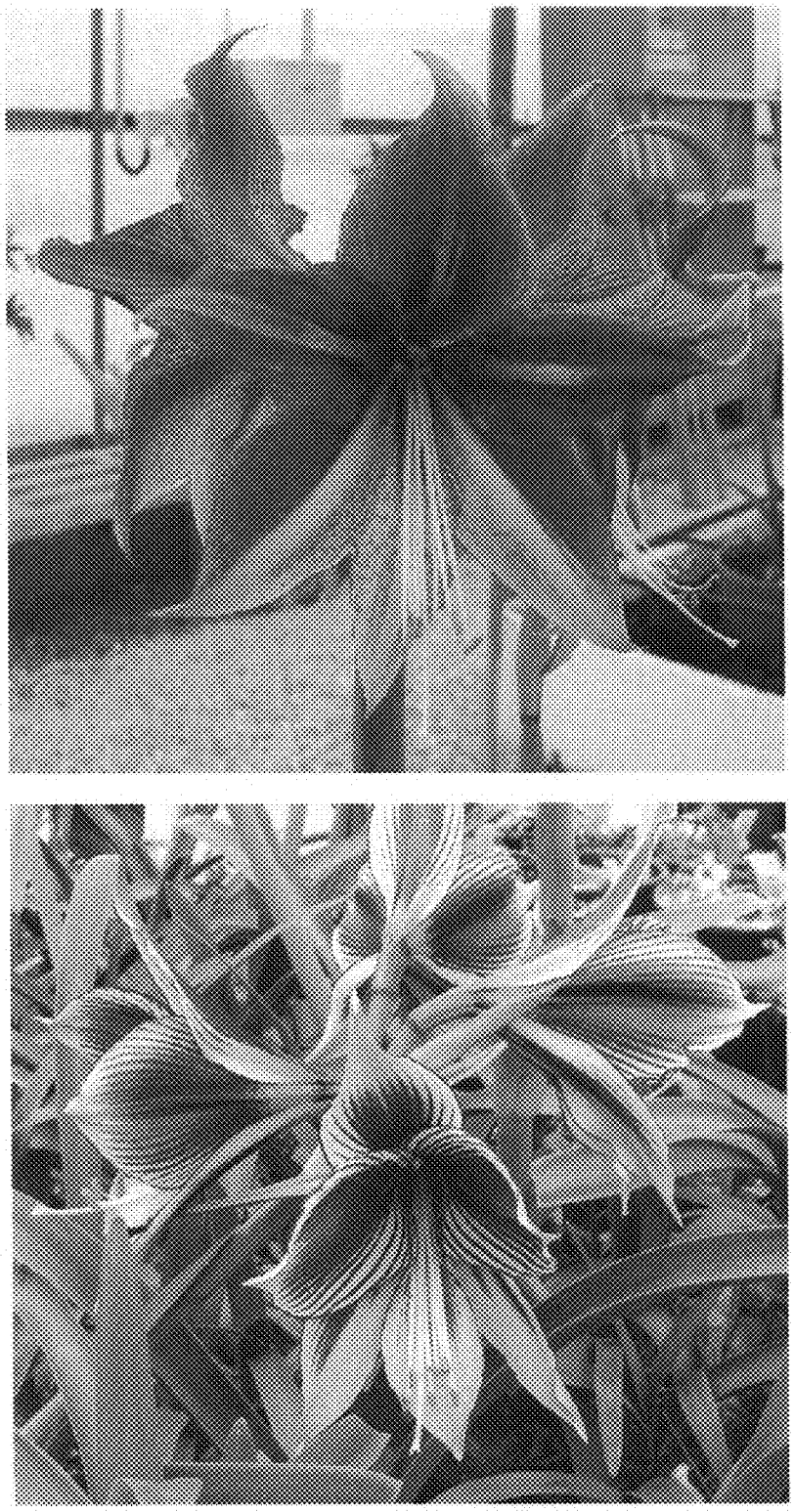
FIG. 2 shows a close-up side view comparison of (1) a typical fully open flower of 'RUBY STAR' (top) to (2) a typical fully open flower of the female parent, the unpatented, wild-type *Hippeastrum papillio* designated WT30.
Figure 3:
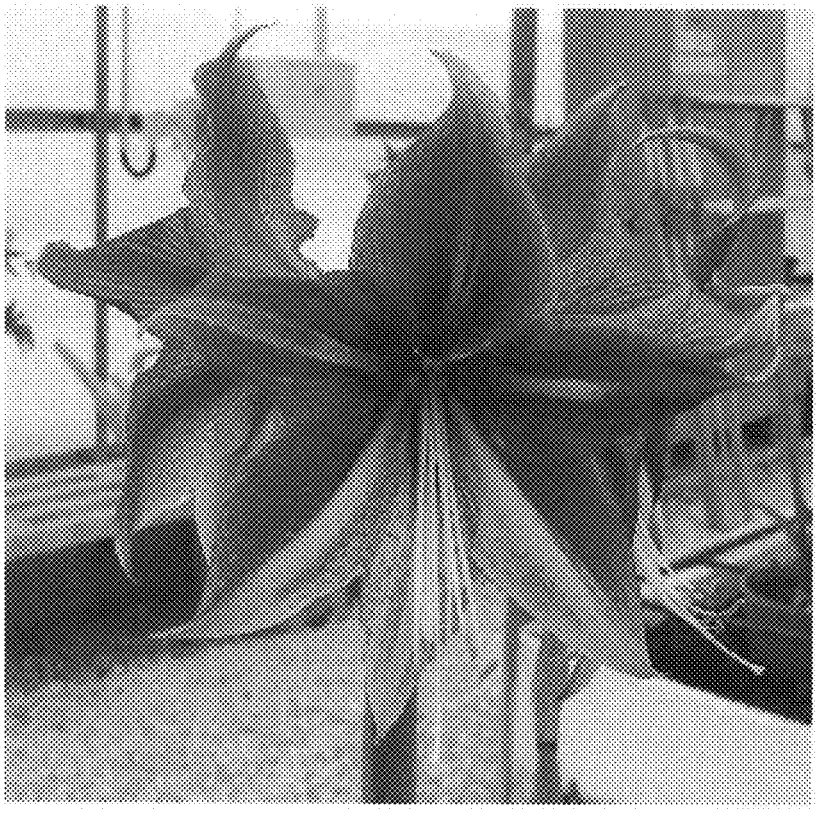
FIG. 3 shows a close-up side view comparison of (1) a typical fully open flower of 'RUBY STAR' (top) to (2) a typical fully open flower of the male or pollen parent, the unpatented interspecific *Hippeastrum* hybrid designated 97/4 (*H. vittatum* 'WHITE'×wild-type *H. cybister* designated WT40).
Figure 3:
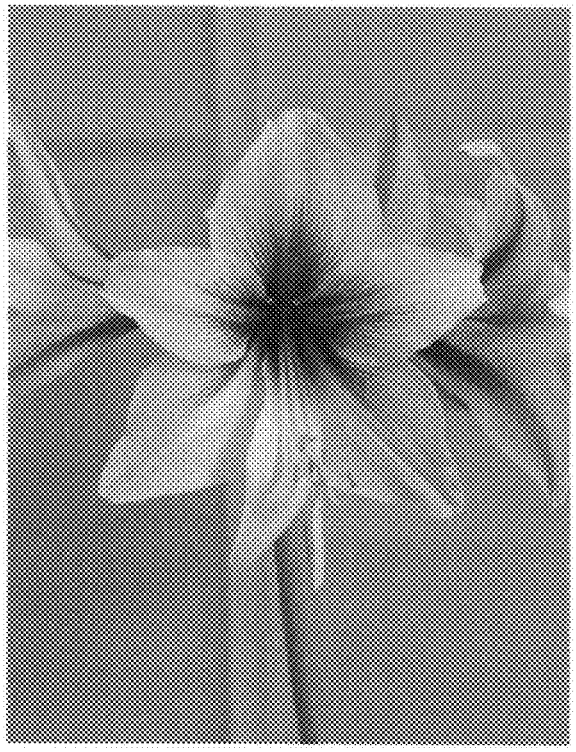
Figure 4:
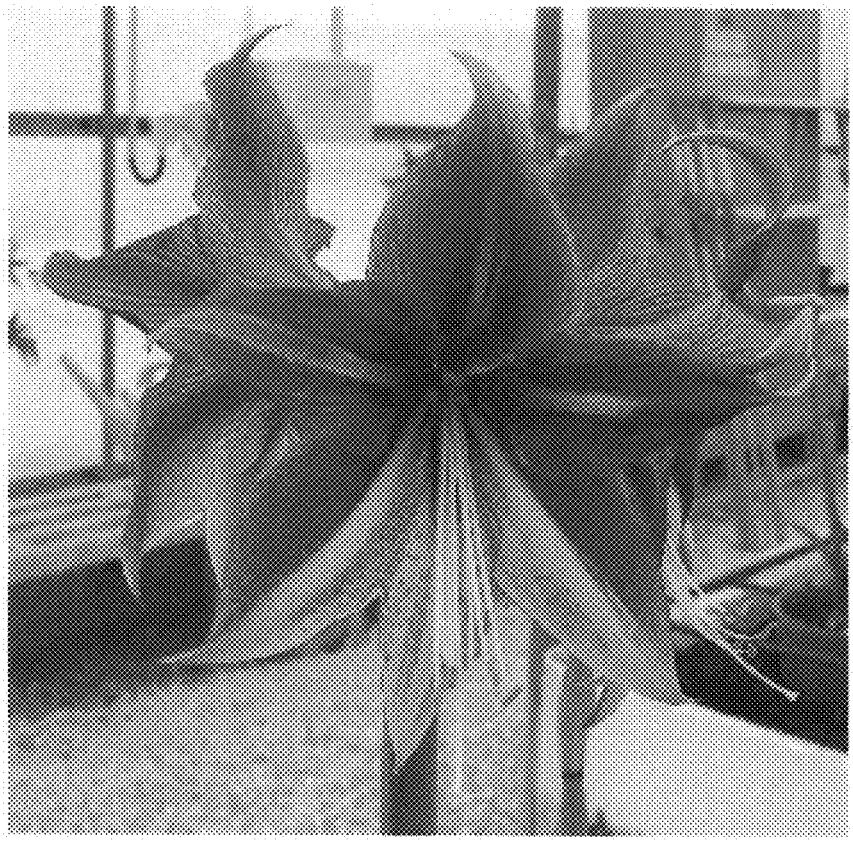
FIG. 4 shows a close-up side view comparison of (1) a typical fully open flower of 'RUBY STAR' (top) to (2) a typical fully open flower of the unpatented, wild-type *Hippeastrum cybister* (WT40) (one of the cultivars crossed to produce the male or pollen parent, the unpatented interspecific *Hippeastrum* hybrid designated 97/4.)
Figure 4:
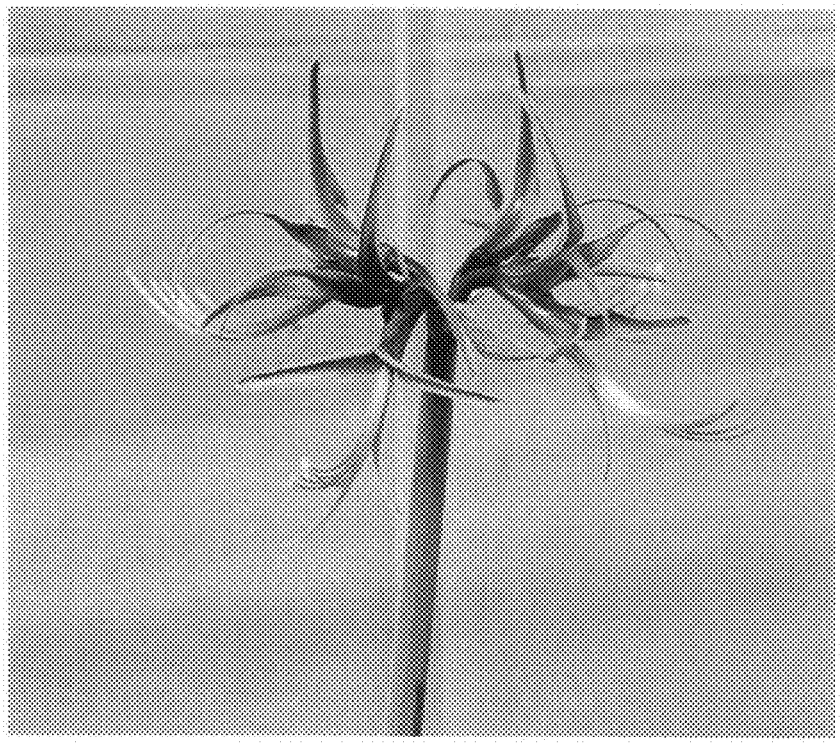
Figure 5:
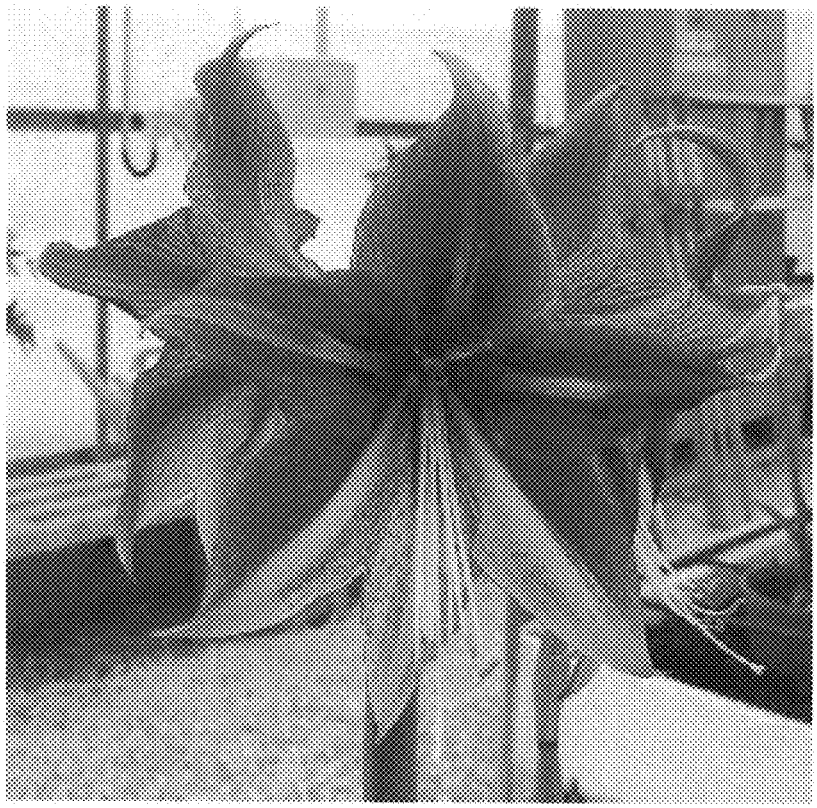
FIG. 5 shows a close-up side view comparison of (1) a typical fully open flower of 'RUBY STAR' (top) to (2) a typical fully open flower of the commercial cultivar *Hippeastrum hybrid* (leopoldii-type) 'Red Lion'.
Figure 5:
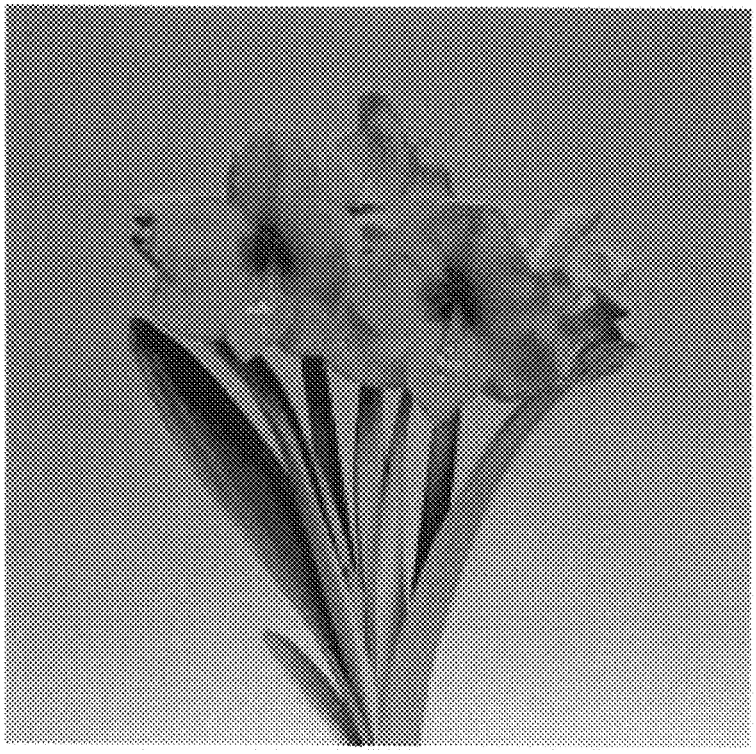

The new *Hippeastrum* 'RUBY STAR' has not been observed under all possible environmental conditions. The phenotype of the new variety may vary with variations in environment such as temperature, light intensity, and day length, without any change in the genotype of the plant.

The aforementioned photographs, together with the following observations, measurements and values describe plants of 'RUBY STAR' as grown in a greenhouse in Bet-Dagan, Israel, under conditions which closely approximate those generally used in commercial practice.

Mother bulbs of 'RUBY STAR' (about 28 to 30 cm in circumference) are cut into 12 vertical segments which are subsequently subdivided into 5 to 6 twin-scale units. The twin-scale units are dipped for 15 minutes in 0.2% BENLATE and 0.5% MARPAN to prevent fungal infection, then the twin-scale units are air dried for 3-4 hours and placed in moist Vermiculite no. 2 (8-10% moisture) and incubated at 22° C. to 24° C. for 3-4 months. The resulting bulblets are planted and grown in raised, heated soil beds (soil temperature maintained at an average temperature of about 20° C. to 22° C.) in coco-peat and Tuff 0.8 (80:20%) and grown for 2 years until they flower for the first time.

Plants of 'RUBY STAR' have been grown in an insect-proof greenhouse, covered with a permanent polycarbonate roof with movable polyethylene curtains, and under 50% shading. Drip irrigation is administered at 80-100 m3/ha and a liquid fertilize is applied of (NPK 5:3:8) 50 ppm. Plants of 'RUBY STAR' are grown with an average winter air temperature of about 12° C. to 25° C. during the day and about 6° C. to 12° C. during the evening and an average summer air temperature of about 22° C. to 38° C. during the day and about 18° C. to 22° C. during the evening. Plants of 'RUBY STAR' reach full growth about 6 to 10 weeks after planting cured bulbs. Quantified measurements are expressed as an average or a range of measurements taken from a number of plants of 'RUBY STAR'. The measurements of any individual plant, or any group of plants, of the new variety may vary from the stated average or range.

Color references are made to The Royal Horticultural Society Colour Chart (R.H.S.), 1986 edition, except where general colors of ordinary significance are used. Color values were taken under daylight conditions at approximately noon in full sunlight in Bet Dagan, Israel.

All of the plants of 'RUBY STAR', insofar as they have been observed, have been consistent in all the characteristics described below.

The age of the 'RUBY STAR' plants described is about 6 to 10 weeks after planting cured bulbs season.

Classification:
*Botanical.*—*Hippeastrum Herb.*
Parentage:
*Female or seed parent.*—unpatented, wild-type *Hippeastrum papillio* designated WT30.
*Male or pollen parent.*—unpatented, interspecific *Hippeastrum* hybrid designated 97/4 (*H. vittatum* 'WHITE'×wild-type *H. cybister* designated WT40).
Propagation:
*Type.*—"Twin-scaling" method (division of the mother bulb into vertical segments and twin-scale units).
Roots:
*Habit and description.*—Fleshy; inserted around basal plate of bulb.
*Length.*—up to 20 cm.
*Diameter.*—2 mm to 4 mm.
*Color.*—off-white, RHS 158 C.
Plant:
*Appearance.*—perennial, herbaceous; 1-3 scapes developing sequentially with a complement of 5 to 8 leaves.
*Growth habit.*—erect.
*Habit.*—leaves are slightly arching and scapes vertical.
*Vigor.*—strong.
*Growth time.*—following asexual propagation, 2 years of growing time are required to produce a flowering plant. Plants of 'RUBY STAR' reach full growth about 6 to 10 weeks after planting of cured bulbs in late autumn.
*Size at maturity.*—Height: 45 to 70 cm. Spread: 50 to 60 cm.
Bulb (described after harvest and curing, before planting):
*Overall shape.*—spherical.
*Shape in cross section.*—rounded.
*Shape in longitudinal section.*—elliptical to oblate.
*Length.*—7.0 to 9.0 cm.
*Diameter.*—9.5 to 10.2 cm.
*Surface.*—irregular.
Color of flesh: yellow-white, closest to RHS 158 C.
Color of dry scale: greyed-orange, RHS 165 B.
*Harvest time of bulbs.*—beginning of August in Bet-Dagan, Israel. Lifted bulbs are dipped for 15-20 minutes in 0.2% BENLET and 0.5% MARPAN solution and then air dried for 10 days.
*Storage time.*—stored in 9° C. from mid August until mid November (10-12 weeks) in Bet-Dagan, Israel.
Leaves:
*Arrangement and attachment.*—basal from scale; single.
*Number per plant.*—typically 5 to 8.
*Overall shape of leaf.*—linear.
*Apex shape.*—acute.
*Base shape.*—parallel.
*Shape of cross-section.*—V-shape.
*Margin.*—entire.
*Margin undulation.*—none.
*Upper surface.*—smooth, medium glossiness. Lower surface: glabrous, very strong glossiness.
*Pubescence.*—none.
*Mature leaf length.*—55 to 65 cm.
*Mature leaf width.*—70 to 80 mm.
*Mature leaf color of upper surface.*—dark green, RHS 137 B;
*Mature leaf color of lower surface.*—dark green, RHS 137 C.
*Venation.*—pattern: parallel, inconspicuous venation.

Inflorescence description:
*Appearance.*—one umbel per scape with 4 or 5 single, star-shaped flowers that open sequentially.
*Natural blooming period.*—in spring in Bet-Dagan, Israel.
*Flowering response time.*—after planting cured bulb, plants typically flower within about 6 to 10 weeks.
*Flowering longevity on the plant.*—8 to 12 days, depending on temperature.
*Flowering longevity as cut flower.*—6 to 9 days.
*Inflorescence fragrance.*—none.
*Inflorescence type.*—umbel.
*Umbel.*—height: 15 to 20 cm. Umbel diameter: 20 to 23 cm.
*Number of flower buds and flowers per umbel.*—4,5 or 6.
Flower bud:
*Shape.*—broad elliptic.
*Length.*—8 to 10 cm.
*Width.*—about 3 cm.
*Texture.*—smooth.
Color of outer side of bract: ground color, yellow-green, between RHS 145 A and RHS 145 B, changing towards opening of the flower into greyed-purple, RHS 185 A.
Color of inner side of bract: ground color, greyed-purple, RHS 185 A with yellow-green central veins, between RHS 145 A and RHS 145 B.
Scape:
*Appearance.*—erect, leafless, hollow.
*Strength.*—strong.
*Twisting.*—slightly twisted towards umbel.
*Shape in cross-section.*—elliptical.
*Length.*—45 to 60 cm.
*Maximum thickness of upper part.*—24 to 26 mm.
*Maximum thickness of middle part.*—26 to 29 mm.
*Maximum thickness of basal part.*—34 to 35 mm.
*Surface.*—glabrous.
*Glaucosity.*—strong.
*Color.*—dark green, RHS 137 C.
*Intensity of anthocyanin coloration at base.*—medium.
Flower:
*Rate of opening.*—flowers fully opened about 2 to 3 days after beginning of tepal separation; all flowers, per umbel, open in about 8 to 14 days.
*Attitude.*—slightly outwards. Shape: star-shaped. Length: 18 to 20 cm. Diameter: 14 to 17 cm. Throat: covered with numerous green-white, RHS 157 D, and greyed-purple, RHS 185 B, hairs.
*Tepals.*—Number and arrangement: slightly overlapping and arranged in an outer whorl of 3 tepals and an inner whorl of 3 tepals. Outer tepals: Overall shape: ovate. Apex: acute with slight twisting of tip. Base: acute. Margin: entire with medium strong undulation. Length: 10 to 13 cm. Width: 50 to 60 mm. Upper surface: smooth; Lower surface: smooth. Main color of upper surface: red, RHS 53 B. Color of middle zone of upper surface: yellow-green, RHS 145 A; Color of veins of upper surface: dark greyed-purple, RHS 185 A. Main color of lower surface: red, RHS 53 B, with yellow-green stripes, RHS 145 B. Color of middle zone of lower surface: dark greyed-purple, RHS 183 B. Inner stepal: Arrangement: one central lower tepal and two lateral tepals. Central tepal: Shape: elliptical. Apex: acute. Base: acute. Margin: entire with weak undulation. Length: 10 to 11 cm. Width: 28 to 30 mm.

Upper surface: smooth; Lower surface: smooth. Main color of upper surface: red, between RHS 53 B and RHS 53 C. Color of middle zone of upper surface: yellow-green, between RHS 145 B and RHS 145 C. Color of veins of upper surface: dark greyed-purple, RHS 185 B. Main color of lower surface: very light yellow-green, RHS 154 D. Color of middle zone of lower surface: dark greyed-purple, RHS 184 B. Color of veins of lower surface: very light yellow-green, RHS 154 D, and light red, RHS 53 D. Lateral tepals: Shape: ovate. Apex: acute with slight twisting of tip. Base: almost right angle. Margin: entire with medium strong undulation. Length: 9 to 11 cm. Width: 40 to 45 mm. Upper surface: smooth. Lower surface: smooth. Main color of upper surface: red, RHS 53 B. Color of middle zone of upper surface: basal part, yellow-green, RHS 145 B, and apical part, dark greyed-purple, RHS 185 A. Color of veins of upper surface: dark greyed-purple, RHS 185 A. Main color of lower surface: red, RHS 53 B, and yellow-green stripes, RHS 145 B. Color of middle zone of lower surface: dark greyed-purple, RHS 183 B. Color of veins of lower surface: dark greyed-purple, RHS 185 A.

*Pedicel.*—Strength: strong. Attitude of flower: semi upright. Length: 45 to 60 mm. Thickness: 6 to 7 mm. Surface: smooth. Color: green, with strong anthocyanin coloration.

Reproductive organs:

*Androecium.*—Stamen: Number: 6. Arrangement: adpressed to lowest tepal, distal ends upwardly curved. Anthers: Color: yellow-green, RHS 150 D, in unripe stage, brown, RHS 200 A, in ripe stage. Shape: elongated. Length: 8 to 10 mm. Filaments: Length: 90 to 105 mm. Thickness: 2 to 3 mm. Color of upper part: very light yellow-green, RHS 145 D. Color of lower part: yellow-green, RHS 145 B. Pollen: Amount: abundant. Color: yellow-green, RHS 145A.

*Gynoecium.*—One pistil, 10 to 13 mm in length. Stigma: Shape: three-lobed. Color: very light yellow-green, RHS 145 D. Style: Length: 10 to 13 mm. Thickness: About 2 mm. Color of upper part: very light yellow-green, RHS 145 D, with some anthocyanin coloration. Color of lower part: light yellow-green, RHS 145 B. Ovary: Color: green, with strong anthocyanin coloration.

Fruit/seed: none.

Disease/pest resistance: none tested or observed.

What is claimed is:

1. A new and distinct *Hippeastrum* interspecific hybrid plant named 'RUBY STAR', as illustrated and described herein.

* * * * *